United States Patent [19]
Scheidegger et al.

[11] Patent Number: 5,290,926
[45] Date of Patent: Mar. 1, 1994

[54] ISOLATED DNA ENCODING PLANT HISTIDINOL DEHYDROGENASE

[75] Inventors: Alfred Scheidegger, Nishinomiya, Japan; Eric R. Ward; John A. Ryals, both of Durham, N.C.; Atsuko Nagai-Hayashi, Amagasaki, Japan

[73] Assignee: Ciba-Geigy Corporation, Ardsley, N.Y.

[21] Appl. No.: 583,892

[22] Filed: Sep. 14, 1990

[51] Int. Cl.$^5$ ..................... C12N 15/29; C12N 15/53
[52] U.S. Cl. .................... 536/23.2; 435/190; 935/9; 935/14
[58] Field of Search .................... 435/69.1–69.9, 435/172.1–172.3, 252.3–252.33, 320.1, 190, 67.1; 536/27

[56] References Cited

U.S. PATENT DOCUMENTS

| | | | |
|---|---|---|---|
| 4,535,060 | 8/1985 | Comai | 435/172.3 |
| 4,751,081 | 6/1988 | Suslow et al. | 424/93 |
| 4,925,374 | 12/1990 | Goodman et al. | 435/172.3 |
| 4,996,155 | 2/1991 | Sick et al. | 435/252.3 |
| 5,013,659 | 5/1991 | Bedbrook et al. | 435/183 |
| 5,073,677 | 12/1991 | Helmer et al. | 800/205 |

FOREIGN PATENT DOCUMENTS

0290406 11/1988 European Pat. Off. .
0360750 3/1990 European Pat. Off. .
0366612 5/1990 European Pat. Off. .

OTHER PUBLICATIONS

Palacios; R., Journal of Biological Chemistry, 251(15):4787–4791.
Shaltiel, S., et al., 1974, Biochemistry, 13(21):4330–4335.
Ullrich, A., et al., 1984, The EMBO Journal 3(2):361–364.
Matthews, B. F., et al., 1988, Plant Molecular Biology Reporter 6(3):137–154.
Mazur, B. J., et al., 1989, Annual Review of Plant Physiology and Plant Molecular Biology 40:441–470.
Scopes, R. K., 1987, Protein Purification: Principles and Practice, 2nd Ed., Springer-Verlag, Preface, p. x and pp. 137–138.
Muflin, B. J., 1980, in The Biochemistry of Plants, vol. 5, Academic Press, Inc., pp. 533–539.
Krishinaswamp, S., et al., 1986, Archives of Biochemistry and Biophysics 246(1):250–262.
Steinrücken, H. C., 1986, Archieves of Biochemistry and Biophysics, 244(1):169–178.
Struhl, K., 1986, Journal of Molecular Biology, 191:221–229.
Swanson, E. B., et al., 1988, Plant Cell Reports, 7:83–97.
Haughn, G. W., et al., 1990, Plant Physiology, 92: 1081–1085.

(List continued on next page.)

Primary Examiner—Robert A. Wax
Assistant Examiner—William W. Moore
Attorney, Agent, or Firm—Shawn P. Foley; Henry H. Nowak

[57] ABSTRACT

The present invention comprises cDNA coding for histidinol dehydrogenase from plants, the final step in histidine biosynthesis. The invention also comprises a novel method of purifying histidinol dehydrogenase from plants to essential honogeneity, the purified histidinol dehydrogenase, an assay for identifying inhibitors of histidinol dehydrogenase, an assay to identify mutants of histidinol dehydrogenase that are not inhibited by inhibitors of wild-type histidinol dehydrogenase, the inhibitors so identified as well as herbicide compositions containing them, the non-inhibited mutants of histidinol dehydrogenase, transgenic crop plants containing the non-inhibited mutants of histidinol dehydrogenase, and methods of treating weeds utilizing the application of histidinol dehydrogenase inhibitors to the transgenic crops containing the non-inhibited mutants of histidinol dehydrogenase.

8 Claims, 6 Drawing Sheets

OTHER PUBLICATIONS

Chavest, P. J., et al., 1990, Plant Cell Reports, 8:643–646.

Kishore, G., et al., 1987, Federation Proceedings 46(6): 2055, abstract No. 754.

Smith, J. K. et al., 1989, Proceedings of the National Academy of Sciences USA, 86:4179–4183.

Parker, W. B., et al., 1990, Proceedings of the National Academy of Sciences, 87:7175–7179.

Rogers, S. G., et al., 1983, Applied and Environmental Microbiology, 46(1):37–43.

DeBlock, M., et al., The EMBO Journal 6(9):2513–2518.

della-Cioppu, G., et al., 1987, Bio/Technology, 5:579–584.

Olszewski, N. E., et al., 1988, Nucleic Acids Research, 16(27):10765–10782.

Lyon, B. R., et al., Plant Molecular Biology, 13:533–540.

Miki, B. L., et al., 1990, Theoretical and Applied Genetics, 80:449–458.

Saxena, P. K., et al., 1990, Plant Physiology, 94:1111–11115.

Hall, L. M., et al., 1990, Plant Physiology 93: 962–966.

Odell, J. M., et al., 1990, Plant Physiology, 94: 1647–1654.

Bottorman, J., et al., 1988, Trends in Genetics, 4(8):219–222.

Shah, D. M., et al., 1986, Science, 233:478–481.

Hilton, J. L., et al., 1965, Archives of Biochemistry and Biophysics, 112:544–547.

McWhorter, C. G., et al., 1967, Physiologia Plantarum, 20:30–40.

Lehninger, A. L., 1975, *Biochemistry*, Second Edition, Worth Publishers, Inc., Chapter 25, pp. 693–724.

Sakihama, *J. of Biochem.*, 93:129–134 (1983).

Dean, *TRAC, Trends in Analytical Chemistry*, 2:80–83 (1983).

Yourno and Ino, J. Biol. Chem., 243:3273–3276 (1968).

Gorisch and Holke, Eur. J. Biochem., 150:305–308 (1985).

Grubmeyer et al., Biochem., 28:8174–8180 (1989).

Bitar et al., Biochem. Biophys. Acta, 493:429–440 (1977).

Shaffer et al., Brookhaven Symp. Biol., 23:250–270 (1972).

Keesey Jr. et al., J. Biol. Chem., 254:7427–7433 (1979).

Dougall and Fulton, Plant Physiol., 42:941–945 (1967).

Negrutiu et al., Mol. Gen. Genet., 199:330–337 (1985).

Heim et al., Plant Physiol., 91:1226–1231 (1989).

Yadava, Mol. Gen. Genet., 170:109–111 (1979).

Wong and Mazelis, Phytochem., 20:1831–1834 (1981).

Wiater et al., Acta Biochim. Polonica, 18:299–307 (1971).

```
  1  AATTCGGCACGAGCCTATTCGCCGGGCGAACACACTCCTATTTGAGCAAACCGGTGAGGA   60
                                                              M

61  TGTCATTCGATCTATCTCGTCTCTCCCTCACTTCCTCGCCTCTCGTTCTCACTC       120
      S  F  D  L  S  R  L  S  L  T  S  S  P  R  L  S  F  L  T  R

121  GCACTGCTACTAAGAAAGGATTCGTTAGGTGTGTTCGATGAAGTCGTACAGATTATCTGAAC 180
      T  A  T  K  K  G  F  V  R  C  S  M  K  S  Y  R  L  S  E  L

181  TTAGTTTCTCTCAAGTTGAGAACTTGAAGGCACGCCCTCGCATTGACTTCTCTTCCATTT  240
      S  F  S  Q  V  E  N  L  K  A  R  P  R  I  D  F  S  S  I  F

241  TCACCACTGTTAACCCAATCATCGACGCTGTTCGTAGCAAAGGAGATACTGCTGTCAAAG  300
      T  T  V  N  P  I  I  D  A  V  R  S  K  G  D  T  A  V  K  E

301  AGTATACAGAGAGATTTGACAAAGTCCAGCTCAATAAAGTGGTGGAGGATGTGTCCGAAC  360
      Y  T  E  R  F  D  K  V  Q  L  N  K  V  V  E  D  V  S  E  L

361  TTGATATCCCTGAGCTCGACTCCGCAGTTAAAGAAGCGTTTGATGTTGCGTATGACAACA  420
      D  I  P  E  L  D  S  A  V  K  E  A  F  D  V  A  Y  D  N  I
```

FIG. 3A

```
421  TTTATGCATTTCACTTTGCCCAAATGTCAACTGAGAAAAGCGTTGAGAATATGAAAGGTG    480
      Y  A  F  H  F  A  Q  M  S  T  E  K  S  V  E  N  M  K  G  V

481  TAAGATGTAAAAGGGTGTCGAGATCTATTGGTTCTGGTTGTCTTTATGTGCCTGGTGGAA    540
      R  C  K  R  V  S  R  S  I  G  S  V  G  L  Y  V  P  G  G  T

541  CTGCTGTTTTGCCATCTACTGCTTTGATGCTTGCTCAGATTGCTCTGGATGTA         600
      A  V  L  P  S  T  A  L  M  L  A  I  P  A  Q  I  A  G  C  K

601  AAACAGTTGTCCTCGCAACTCCACCAACTAAGGAAGGAAGCATATGTAAGGAGGTGCTGT    660
      T  V  V  L  A  L  P  P  T  K  E  G  S  I  C  K  E  V  L  Y

661  ATTGTGCCAAGAGGGCTGGTGTAACTCACATTCTTAAAGCTGGTGGAGCACAGGCTATAG    720
      C  A  K  R  A  G  V  T  H  I  L  K  A  G  G  A  Q  A  I  A

721  CTGCCATGGCCTGGGGGACAGATTCTTGTCCTAAGGTTGAGAAGATTTTTGGTCCTGGGA    780
      A  M  A  W  G  T  D  S  C  P  K  V  E  K  I  F  G  P  G  N
```

FIG. 3B

```
781   ATCAGTATGTTACAGCTGCTAAGATGATTCTGCAAAACAGCGAGGCAATGGTTTCGATTG   840
        Q  Y  V  T  A  A  K  M  I  L  Q  N  S  E  A  M  V  S  I  D

841   ATATGCCTGCTGGCCCTTCAGAAGTTCTTGTTATCGCTGATGAACATGCTAGTCCAGTTT   900
        M  P  A  G  P  S  E  V  L  V  I  A  D  E  H  A  S  P  V  Y

901   ACATTGCAGCCGACTTACTTTCTCAGGCTGAGCATGGTCCAGATAGTCAGGTTGTTCTTG   960
        I  A  A  D  L  L  S  Q  A  E  H  G  P  D  S  Q  V  V  L  V

961   TTGTTGTAGGCGATGGTGTAAATCTCAAAGCCATCGAAGAAGAAATTGCTAAACAATGCA  1020
        V  V  G  D  G  V  N  L  K  A  I  E  E  E  I  A  K  Q  C  K

1021  AAAGCCTTCCTAGAGGCGAGTTTGCTTCAAAAGCTCTAAGTCACAGCTTCACAGTATTTG  1080
        S  L  P  R  G  E  F  A  S  K  A  L  S  H  S  F  T  V  F  A

1081  CTCGAGATATGATTGAGGCAATAACTTTCTCAAACCTGTATGCACCTGAACACTTGATCA  1140
        R  D  M  I  E  A  I  T  F  S  N  L  Y  A  P  E  H  L  I  I

1141  TCAATGTCAAAGACGCTGAGAAATGGGAGGGACTGATAGAGAACGCAGGTTCGGTTTTCA  1200
        N  V  K  D  A  E  K  W  E  G  L  I  E  N  A  G  S  V  F  I
```

FIG. 3C

```
1201  TAGGGCCGTGGACTCCTGAGAGTGTTGGTGATTACGCGAGCGGGACAAACCACGTTCTTC  1260
       G   P   W   T   P   E   S   V   G   D   Y   A   S   G   T   N   H   V   L   P

1261  CAACGTACGGGTATGCGAGAATGTATACAGTGGCGTCTCTCGACTCTCTTCCTGAAGTTCA  1320
       T   Y   G   Y   Y   A   R   M   Y   S   G   V   S   L   D   S   F   L   K   F   M

1321  TGACTGTACAGTCCTTGACAGAGGAAGGTCTGCGAAACCTTGGTCCGTATGTTGCGACTA  1380
       T   V   Q   S   L   T   E   E   G   L   R   N   L   G   P   Y   V   A   T   M

1381  TGGCTGAAATTGAAGGTCTAGATGCACACAAGAGAGCCGTCACTCTCAGACTCAAGGATA  1440
       A   E   I   E   G   L   D   A   H   K   R   A   V   T   L   R   L   K   D   I

1441  TCGAAGCCAAACAGACCCAAACAAAGTGAAATGGCTGTCTTCATATTCAAAATGAGG  1500
       E   A   K   Q   T   Q   T   K   *

1501  TGACATTGGTTTAAAGAGATAATAATAAGAATATAAGAGATGTTGTAACACTCT  1560

1561  CTGTCATAAATCTGGATTTTCTTTCATTATTGAAATTTGAATCCCTTTCACGCGT  1613
```

FIG. 3D

ISOLATED DNA ENCODING PLANT HISTIDINOL DEHYDROGENASE

BACKGROUND OF THE INVENTION

Histidinol dehydrogenase [L-Histidinol-NAD Oxido-Reductase (EC 1.1.1.23)] catalyzes the final two steps in the biosynthesis of the amino acid histidine. This reaction is an oxidation of histidinol to histidinal to histidine, which is coupled to reduction of two moles of the required cofactor NAD per mole of histidine formed.

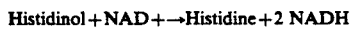

Histidinol+NAD+→Histidine+2 NADH

While the enzyme and gene encoding it have been well characterized in the bacteria *Salmonella typhimurium* [Yourno and Ino, J. Biol. Chem. 243:3273-3276 (1968); Gorisch and Holke, Eur. J. Biochem. 150:305-308 (1985); and Grubmeyer et al., Biochem. 28:8174-8180 (1989)] and *Escherichia coli* [Bitar et al., Biochem. Biophys. Acta 493:429-440 (1977)] and the yeast *Saccharomyces cereviseae* [Schaffer et al., Brookhaven Symp. Biol. 23:250-270 (1972); and Keesey et al., J. Biol. Chem. 254:7427-7433 (1979)], this enzyme has not been previously purified to homogeneity from any plant sources. This is in part because enzymes for primary metabolic functions such as amino acid biosynthesis are especially difficult to purify due to their low concentration in the source tissue. In plants, this difficulty is compounded by the existence of phenolic compounds and other secondary metabolites that can react with proteins throughout their purification.

Histidine biosynthesis in general in higher plants has not been studied well. Some evidence for the existence in plants of a biosynthetic pathway similar to that in microorganisms has been obtained from in vivo experiments using various different plants and a blue-green algae [Dougall and Fulton, Plant Physiol. 42:941-945 (1967); Negrutiu et al., Mol. Gen. Genet. 199:330-337 (1985); Helm et al., Plant Physiol. 91:1226-1231 (1989); Yavada, Mol. Gen. Genet. 170:109-111 (1979)].

Histidinol dehydrogenase activity has been detected in ten different plant species: asparagus, cabbage, cucumber, egg plant, lettuce, radish [Wong and Mazalis, Phytochrom. 20:1831-1834 (1981)], rose, squash [Wong and Mazalis, Phytochem. 20:1831-1834 (1981)], turnip [Wong and Mazalis, Phytochem. 20:1831-1834 (1981)], and wheat [Wong and Mazalis, Phytochem. 20:1831-1834 (1981) and this work] and in 5 preparations of distinct cell differentiation: germ [[Wong and Mazalis, Phytochrom. 20:1831-1834 (1981)] and this work), root [Wong and Mazalis, Phytochrom. 20:1831-1834 (1981)], fruit [Wong and Mazalis, Phytochrom. 20:1831-1834 (1981) and this work], shoot, and cultured cell.

Only a few attempts have been made to study the enzymes involved in histidine (His) biosynthesis in higher plants. The hitherto impossible task of purifying to homogeneity any histidine biosynthesis enzyme from plants seems to be the limiting step in biochemical investigations. In crude extracts from shoots of barley, oats and peas, the activities of ATP-phosphoribosyl transferase, imidazoleglycerol phosphate dehydratase and histidinol phosphate phosphatase were detected [Wiater et al., Acta Biochim. Polonica 18:299-307 (1971)]. Histidinol dehydrogenase activity has been found in crude extracts of different plant species [Wong et al., Phytochem. 20:1831-1834 (1981)]. These data suggest that histidine biosynthesis in plants follows the same pathway as in microorganisms, although no protein has ever been isolated from plants and identified as an enzyme involved directly in histidine biosynthesis.

The pathways for biosynthesis of the ten amino acids essential to the human diet are of special interest as targets for development of novel inhibitory compounds that could act as herbicides. This interest is due to the likelihood that a specific inhibitor of any enzyme from these pathways will be completely non-toxic to vertebrates, which lack the biosynthetic pathways for the essential amino acids.

SUMMARY OF THE INVENTION

The present invention comprises cDNA coding for histidinol dehydrogenase from plants, the final step in histidine biosynthesis.

The invention also comprises a novel method of purifying histidinol dehydrogenase from plants to essential homogeneity comprising:

(a) exposing a protein extract to an ion exchange chromatography column to produce a first eluate in the presence of a linear gradient;

(b) exposing the first eluate to an affinity chromatography column to produce a second eluate in the presence of a displacing solvent, wherein said affinity chromatography column comprises a ligand specific for histidinol dehydrogenase;

(c) storing the second eluate.

Another aspect of the present invention is the purified histidinol dehydrogenase, preferably having the amino acid sequence identical to or substatiolly homologous to the amino acid sequence of FIG. 3.

Another aspect of the present invention is an assay to identify inhibitors of histidinol dehydrogenase activity comprising:

(a) incubating a first sample of histidinol dehydrogenase and its substrate;

(b) measuring an uninhibited reactivity of the histidinol dehydrogenase from step (a);

(c) incubating a first sample of histidinol dehydrogenase and its substrate in the presence of a second sample comprising an inhibitor compound;

(d) measuring an inhibited reactivity of the histidinol dehydrogenase from step (c); and (e) comparing the inhibited reactivity to the uninhibited reactivity of the histidinol dehydrogenase.

Another aspect of the present invention is an assay to identify less functional histidinol dehydrogenase mutants comprising:

(a) incubating a first sample of histidinol dehydrogenase and its substrate in the presence of a second sample comprising a histidinol dehydrogenase inhibitor;

(b) measuring an unmutated reactivity of the histidinol dehydrogenase from step (a);

(c) incubating a first sample of a mutated histidinol dehydrogenase and its substrate in the presence of a second sample comprising a histidinol dehydrogenase inhibitor;

(d) measuring a mutated reactivity of the mutated histidinol dehydrogenase from step (c); and (e) comparing the mutated reactivity to the unmutated reactivity of the histidinol dehydrogenase.

Other aspects of the present invention are the inhibitors so identified as well as herbicide compositions containing them, the non-inhibited mutants of histidinol dehydrogenase, transgenic crop plants containing the non-inhibited mutants of histidinol dehydrogenase, and methods of treating weeds utilizing the application of histidinol dehydrogenase inhibitors to the transgenic crops containing the non-inhibited mutants of histidinol dehydrogenase.

DESCRIPTION OF THE FIGURES

FIGS. 3A, 3B, 3C and 3D together depict the entire amino acid and nucleotide sequence for histidinol dehydrogenase from cabbage. Amino acids are represented by the standard one letter designations, nucleotides are represented by the standard letter designations where A is adenine, T is thymidine, C is cytosine, G is guanine, H is selected from thymidine or cytosine, and Y is selected from adenine, thymidine and cytosine.

DETAILED DESCRIPTION OF THE INVENTION

Figure 1:
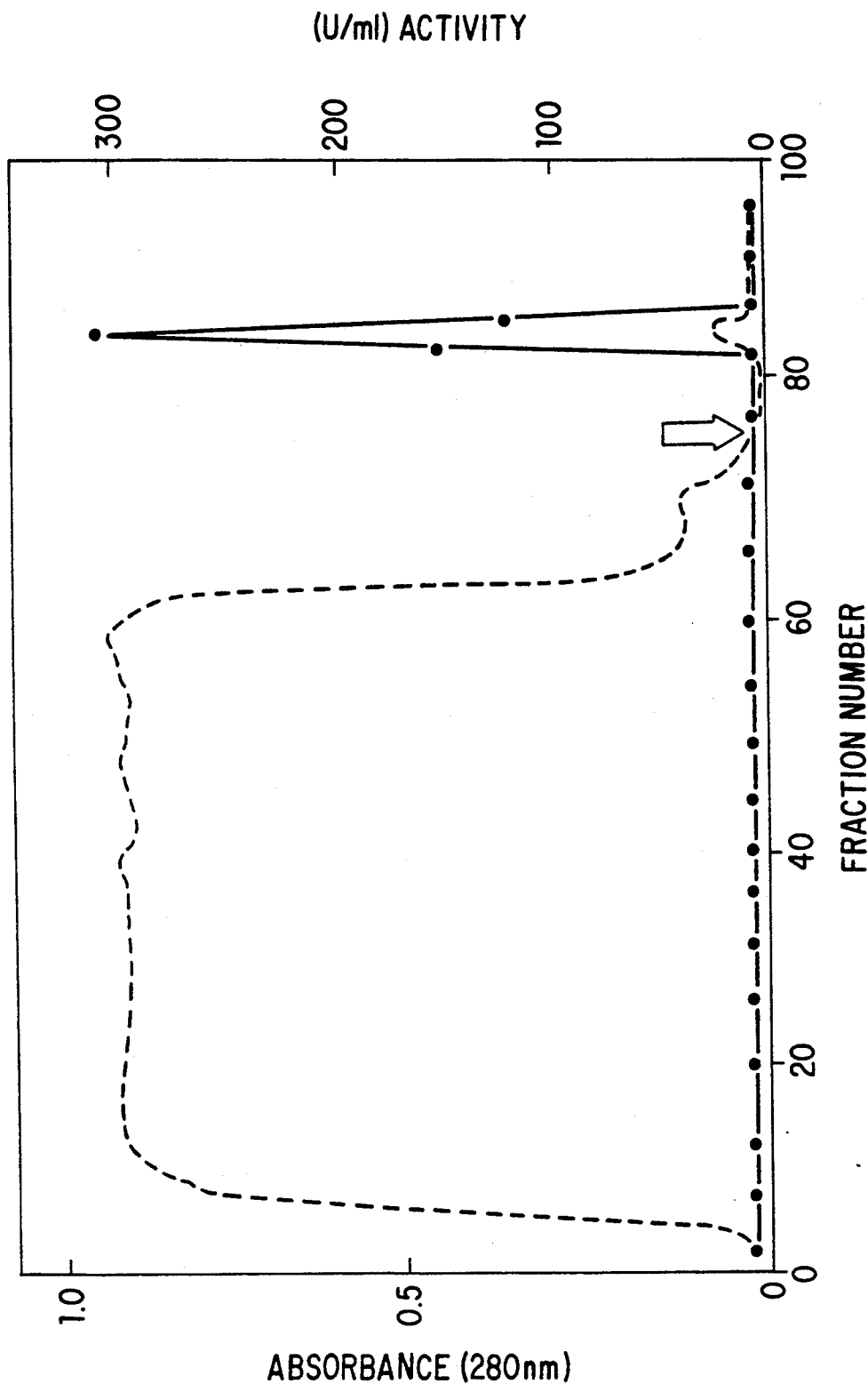
FIG. 1: Histidinol-Sepharose-4B affinity chromatography. (●—●) Protein concentration represented by the absorption at 280 nm;(o—o)histidinol dehydrogenase activity expressed in U/ml. The affinity column was washed with 10 mM Tris/HCl buffer, pH7.3 containing 140 mM NaCl until all non-adsorbed protein was eluted (at fraction No. 75). The arrow at fraction No. 76 indicates the start of the elution with 50 mM Tris/HCl buffer, pH 7.3 containing 700 mM imidazole.

To assist in interpreting the meaning and scope of the present invention, the following terms are intended to have the meanings as described below, unless otherwise indicated. All references cited in this application are hereby incorporated by reference for their relevant teachings.

Coding DNA Sequence: A DNA sequence which, when transcribed and translated, results in the formation of a cellular polypeptide.

Gene: A discrete chromosomal region comprising regulatory DNA sequences responsible for the control of expression, i.e., transcription and translation, and of a coding sequence which is transcribed and translated to give a distinct polypeptide.

Histidinol Dehydrogenase Inhibitory Effective Amount or Significant Decrease in Histidinol Dehydrogenase Activity: A significant decrease in the ability of histidinol dehydrogenase to convert substrates such as histidinol into products such as histidine as measured by quantifying enzymatic activity as generally known to those of skill in the art, including equilibrium constants, reaction velocities of the appearance of reaction products or the consumption of reaction substrates, reaction kinetics, thermodynamics of reaction, spectrophotometric analysis of reaction products, detection of labelled reaction components, etc, with the preferred method measurement being the spectrophotometric measurement of NAD+ as a reaction byproduct. A significant decrease in enzyme activity is any decrease that is larger than the margin of error inherent in the measurement technique, preferably a decrease by 50 percent, more preferably a decrease by 90%, more preferably a decrease by 99%, and most preferably a decrease to essentially undetectable levels of enzyme activity.

Substantial Sequence Homology: Substantial functional and/or structural equivalence between sequences of nucleotides or amino acids. Functional and/or structural differences between sequences having substantial sequence homology will be de minimis. The sequences that differ from the natural sequences are usually variants of the natural sequence. A variant of a natural sequence is a modified form of the natural sequence that performs the same function. The variant may be a mutation, or may be a synthetic sequence. A de minimis functional difference results from a nucleotide or amino acid sequence that codes for a protein having essentially the same characteristics as the native protein. Such characteristics can include, for example, immunological reactivity, enzyme activity, structural protein integrity, etc. Structural differences are considered de minimis if there is a significant amount of sequence overlap or similarity between two or more different sequences or if the different sequences exhibit similar physical properties. In the case of a nucleotide sequence, the different sequences will preferably have at least 60 percent, more preferably 75 percent, most preferably 90 percent or more sequence similarity between them. In the case of amino acid sequences, the different sequences have at least 70 percent, more preferably 80 percent, more preferably 90 percent, and most preferably at least 99 percent or more similarity between the polypeptides coded for by the amino acid sequences. Physical properties that may be similar include, for example, electrophoretic mobility, chromatography similarities, sediment gradient coefficients, spectrophotometric properties, etc.

Transgenic Plant: A plant having stably incorporated exogenous DNA in its genetic material. Various different methods of introducing the exogenous DNA into protoplasts are known in the art and can be used to produce the transgenic protoplasts, transgenic cells or transgenic plants of the present invention.

Weeds: Any undesired species of plant growing among a culture of cultivated plants such as crops, preferably any individual of a species that is heterogeneous to the species of a homogenous population of plants.

The present invention relates to methods of purifying a previously unpurified protein from plants, the protein purified by such a method, DNA coding for such a protein, methods of using the protein and DNA to assay for specific inhibitors of the protein, and methods of using the specific inhibitors to assay for altered forms of the protein that are less functional forms of the protein so as to produce an insensitivity to the inhibitors.

The method of purification utilizes an affinity chromatography column that is specific for histidinol dehydrogenase. Various known methods can be employed previous to and subsequent to the affinity chromatography to produce a crude extract to apply to the affinity column and to characterize and store the protein isolated by the affinity column.

Such previous steps can include homogenization, filtration, centrifugation, ammonium salt precipitation, desalting, ion exchange chromatography, sonication, etc. Preferably, the plant tissue from which the histidinol dehydrogenase is obtained, is homogenized using a blender. The homogenate is then preferably passed through course filtration such as a filtration cloth. The filtrate is then preferably adequately centrifuged, preferably at about 30,000 x g for at least 20 minutes. The supernatant is then preferably precipitated using ammonium sulfate at from about 40 to 70% saturation, more preferably at about 45 to 60% saturation, and the precipitate is collected and desalted using an appropriate desalting technique such as dialysis or gel filtration, preferably using gel filtration with G-25 Sephadex with about 50 mM TRIS/HCL at pH from about 7 to 7.5, preferably pH 7.4.

The desalted protein extract can then be further prepared for affinity chromatography using an appropriate ion exchange column. A preferred ion exchange column is a Diethyl-amino-ethyl (DEAE) derivatized resin, such as DEAE-cellulose, more preferably DEAE-Toyopearl, equilibrated with a suitable buffer such as the buffer used in the desalting step, most preferably 50 mM TRIS/HCL at about pH 7.4. Elution from the ion exchange column can be accomplished using a linear gradient containing the equilibration buffer and a suitable salt gradient. A preferred salt gradient is NaCl from 0 to at least 500 mM. The eluate from the ion exchange column is then an appropriate crude extract for application to the affinity chromatography column.

Appropriate ligands for the chromatography column are any substrate specific for the enzyme, histidinol dehydrogenase, that is to be isolated. Attachment of the ligand to the column resin will preferably occur at a position on the ligand that will not significantly interfere with the binding of the ligand to the enzyme to be isolated. Preferred ligands for histidinol dehydrogenase are therefore histidinol and histidinal, more preferably histidinol. Any suitable resin may be used to attach the ligand, with a preferred resin being Sepharose-4B. Methods of attaching ligands to chromatography resins are generally known in the art.

A preferred method of preparing a suitable affinity column resin is as follows. Sepharose-4B is activated with epichlorohydrin as previously described [Matsumoto et al., J. Biochem. 85:1091-1098 (1979)]. Epoxyactivated Sepharose-4B gel is suspended in 0.1N NAOH containing 0.5 g glucose per g of gel and incubated at 40° C. on a shaker for 24 h [Kanamori et al., J. Chromatog. 363:231-242 (1986). After washing extensively with water, the gel is suspended in prechilled sodium metaperiodate and the suspension shaken for 1 h at 40° C. The gel is washed with water, suspended in 0.1M HCl and incubated at room temperature for 1 h. Again, the gel is washed extensively with water, followed by thorough washing with 10 mM sodium phosphate buffer, pH 7.0 at room temperature.

The formyl carrier gel is suspended in 10 mM sodium phosphate buffer, pH 7.0 containing 100 mM of histidinol dihydrochloride, which is previously neutralized with NAOH, and the suspension incubated at 40° C. overnight. Five milligrams of sodium cyanoborohydride per g of gel is then added to the suspension and incubated with shaking at room temperature for 6 h. The gel is extensively washed with distilled water and treated with 5 mg sodium borohydride per g of gel for 3 h at 4° C. to convert the remaining formyl groups into hydroxymethyl groups.

After preparation of a suitable affinity chromatography column resin, the resin is placed in a suitable column, preferably about 2.5×8 cm. The crude extract of protein is placed on the affinity column and preferably extensively washed with a suitable buffer, preferably containing an adequate ionic strength of salt, e.g., 10 mM TRIS/HCl buffer, about pH 7.3, containing about 100 to 200 mM NaCl, preferably about 140 mM NaCl. The bound enzyme can be eluted using a suitable displacing solvent. A suitable displacing solvent is one containing a substance that will have an affinity to the enzyme to be isolated that is similar to the ligand used in the affinity column. When the enzyme is histidinol dehydrogenase and the ligand is histidinol, a preferred displacing solvent is one containing imidazole, more preferably one containing about 50 mM TRIS/HC1, pH about 7.3, and imidazole.

Subsequent to the affinity chromatography methods can be employed to characterize and store the protein isolated by the affinity column. These include desalting the eluate from the affinity column into a suitable buffer to remove the displacing solvent. The desalted protein can then be further characterized or concentrated and stored cryogenically, preferably below −50° C., more preferably at about −80° C.

The protein can be characterized using standard techniques such as gel filtration (molecular mass), paolyacrylamide gel electrophoresis [Laemmli, Nature 227:680-685 (1970)] (purity and molecular weight), isoelectric focusing (isoelectric point), amino acid sequencing, appropriate enzyme assays (to measure enzymatic activity), etc.

The enzyme activity is assayed spectrophotometrically by measuring the increase in absorbence at 340 nm due to the reduction of NAD+in a Hitachi U-3120 spectrophotomer. The reaction mixture contained 150 mM Gly/NaOH buffer, pH 9.2, 0.5 mM, MnCl , 2 mM NAD+, 5 mM histidinol, and 2-5 mU of enzyme sample in total volume of 0.5 ml. The reaction is started with the addition of histidinol, and incubated at 30° C. A reference sample containing water instead of histidinol is always run. One unit of enzyme catalyzes the formation of 2 μmol of NADH per min under the assay conditions.

In some experiments the activity is also followed by measuring the formation of His with a Hitachi L-850 amino acid analyzer. The enzyme reaction is terminated with formic acid (final concentration, 30%). The sample is then evaporated, and the precipitate dissolved in 0.2N HC1. This preparation is used for His analysis, amino acid sequencing, enzymatic activity, etc.

Determination of amino acid sequencing can be accomplished by known methods, e.g., manual or automated Edman degradation reaction using commercially available instrumentation (Applied Biosystems, Foster City, Calif.). Amino acid sequencing can be performed on the entire full length protein, or sequencing can be performed on fragments or portions of the protein. Such fragments include N-terminal sequencing, sequencing after digestion with Lys-C (Wako Pure Chemical Co., Osaka, Japan), sequencing after digestion with cyanogen-bromide etc.

Using the amino acid sequence(s), portions of the amino acid sequence that display minimal degeneration of the nucleotide sequences coding for the protein can be used to synthesize oligonucleotide probes. The oligonucleotide probes can be synthesized by phosphoramidite chemistry, e.g., as performed by an Applied Biosystems 380B DNA synthesizer (Foster City, Calif.) using reagents available from the manufacturer.

Examples of the useful portions of the amino acid sequence obtained from cabbage that can be used to synthesize oligonucleotide probes include:

| Lys-C #17 | TELSFAK |
| --- | --- |
| Lys-C #18 | TVVLATPPTK |
| Lys-C #32 | EAFDVAYDNIYAFHLAQK |
| Lys-C #45 | KFMTVQSLTEEGLRNLGPYVA TMAEIEGLDA |
| Lys-C #48 | ALSHSFTVFARDMIEAITFSN LYAPEK |
| CNBr #6 | MAEIEGLDAHKRAVTLR?KDIE |
| CNBr #18 | LAIPANIAGRKTVVLATP |
| N-terminal | MKIYRLSELSF?NVENLKAR? ?ID | wherein the amino acid terminology is the standard abbreviations.

After labelling with P-32, these oligonucleotide probes can be used to probe a cDNA library of the MRNA from the organism from which the histidinol dehydrogenase is obtained. Such a library (a cDNA library) of poly A(+) RNA from the source organism can be constructed in an appropriate cloning vector, preferably a cloning vector such as lambdaZAPII (available from Stratagene, La Jolla, Calif. using the Uni-ZAPXR cDNA kit, also available from Stratagene) utilizing methods that are known in the art. Positive hybridization of the oligonucleotide probes to a cDNA clone from the library identifies that clone as potentially containing the nucleotide sequence corresponding to the amino acid sequence for histidinol dehydrogenase.

Alternatively, total DNA from the cDNA library can be prepared and used as a template for a PCR reaction with primers representing low degeneracy portions of the amino acid sequence. Preferably, the primers used will generate PCR products that represent a significant portion of the nucleotide sequence. Preferred primers that can be used to probe total DNA from the cDNA library include:

| EW25 | 5' TTAAGATTCTAYGAYAAYATHTAYGC 3' |
| --- | --- |
| JR03 | 5' CCYTCDATYTCNGCCAT 3' | where D indicates any the bases A, T, or G; H indicates the bases A, T, or C; R indicates the purines A or G; Y indicates the pyrimidines T or C. The PCR products can be further probed to determine if they correspond to a portion of the histidinol dehydrogenase gene using a synthetic oligonucleotide probe corresponding to an amino acid fragment sequence located in the interior or middle region of the histidinol dehydrogenase protein. An example of such a probe would include the $^{32}$P labelled probe represented by the formula:

JR02 5' ATNGCYTCDATCATRTC 3' where D indicates any the bases A, T, or G; H indicates the bases A, T, or C; R indicates the purines A or G; Y indicates the pyrimidines T or C.

The PCR product can thus be used, for example, to select and isolate further DNA clones using standard techniques (Maniatis et al., *Molecular Cloning: A Laboratory Manual*, Cold Spring Harbor Laboratory, Cold Spring Harbor, N.Y. (1982). Nucleotide sequencing of the full length DNA coding for histidinol dehydrogenase can then be obtained using standard techniques (Maxam and Gilbert, Proc. Nat. Acad. Sci. USA 74:560-564 (1977); and Sanger, Proc. Nat. Acad. Sci. USA 74:5463-5467 (1977)] or using commercially available nucleotide sequencing instrumentation (available from Applied Biosystems, Foster City, Calif. and Dupont, Wilmington, Del.).

The purified histidinol dehydrogenase can then be used in an assay to identify inhibitors of the histidinol dehydrogenase activity. Alternatively, purified histidinol dehydrogenase can be obtained from transgenic expression of the DNA coding for the enzyme, i.e., placing the gene for histidinol dehydrogenase into an appropriate bacterial, yeast or other cell expression system.

An assay to identify inhibitors of histidinol dehydrogenase activity comprises:

(a) incubating a first sample of histidinol dehydrogenase and its substrate;

(b) measuring an uninhibited reactivity of the histidinol dehydrogenase from step (a);

(c) incubating a first sample of histidinol dehydrogenase and its substrate in the presence of a second sample comprising an inhibitor compound;

(d) measuring an inhibited reactivity of the histidinol dehydrogenase from step (c); and (e) comparing the inhibited reactivity to the uninhibited reactivity of the histidinol dehydrogenase.

Suitable histidinol dehydrogenase for the above assay can be obtained using the purification methods of the present invention. Suitable substrates are histidinol or structural analogs that are capable of being converted into an analog of histidine by the histidinol dehydrogenase enzyme, with the preferred substrate being histidinol. Preferably, the substrate is at a concentration of about 1 to about 100 mM, more preferably at about 1 to about 10 mM, most preferably at about 5 mM.

In addition to the histidinol dehydrogenase enzyme and a suitable substrate, the reaction mixture can contain a suitable buffer, suitable cofactors and suitable divalent cations as a cofactor. A suitable buffer includes any suitable biological buffer that can provide buffering capability at a pH conducive to the reaction requirements of the enzyme. Preferably, the buffer provides buffering capability in the pH range 7.5 to 10.0, more preferably in the pH range of about 9.1 to about 10.0, most preferably at a pH of about 9.2, e.g., 150 mM Gly/NaOH (glycine/sodium hydroxide) at pH 9.2. A preferred cofactor for the histidinol dehydrogenase enzyme is NAD, preferably at a concentration of about 1 to about 100 mM, more preferably at about 2 mM. Preferably, the divalent cation is a divalent metal cation, more preferably manganese. The reaction is carried out at a suitable temperature to allow the reaction to proceed. Such a suitable temperature is about 4° C. to about 40° C., more preferably from about room temperature to about 35° C., most preferably at about 30° C. The most preferred reaction mixture contains 150 mM Gly/NaOH buffer, pH 9.2, 0.5 mM, MnCl$_2$, 2 mM NAD+, 5 mM histidinol, and 2-5 mU of enzyme sample in total volume of 0.5 ml at 30° C. Preferably, the reaction is started with the addition of histidinol.

Uninhibited reactivity of the histidinol dehydrogenase is any measure of enzymatic activity of the histidinol dehydrogenase enzyme while in the presence of a suitable substrate. Such measures of enzymatic activity are generally known to those of skill in the art, including equilibrium constants, reaction velocities of the appearance of reaction products or the consumption of reaction substrates, reaction kinetics, thermodynamics of reaction, spectrophotometric analysis of reaction products, detection of labelled reaction components, etc. See, generally, Segel, *Biochemical Calculations*, 2nd Edition, John Wiley and Sons, New York (1976); Suelter, *A Practical Guide to Enzymology,* John Wiley and Sons, New York (1985). The preferred method of measuring enzymatic activity is spectophotometrically by measuring the increase in absorbence at 340 nm due to the resuction of NAD+, e.g., using a Hitachi U-3120 spectrophotometer.

Suitable inhibitor compounds are identified using the above methods. To date at least seven compounds have been so identified.

Inhibited reactivity is determined in the same manner as uninhibited reactivity with the addition of an inhibitor of histidinol dehydrogenase. The concentration of the inhibitor may vary depending on the inhibitory activity, but generally it will be in an amount ranging from about 10 nm to about 200 mM, more preferably about 0.1 mM to about 100 mM, more preferably about 1 to about 10 mM. Generally, the histidinol or other substrate will be added to a mixture containing the enzyme and inhibitor and then an enzyme activity determined as described previously.

Comparing the inhibited reactivity to the uninhibited reactivity of the histidinol dehydrogenase includes determining whether a significant decrease in enzyme activity is observed in the inhibited reactivity compared to the uninhibited reactivity. A significant decrease is a decrease in enzymatic activity that is larger than the margin of error inherent in the measurement technique, preferably a decrease by about 50% of the activity in the absence of the inhibitor, more preferably a decrease by about 90%, more preferably a decrease by about 99%, most preferably a decrease to a level of enzymatic activity that is essentially undetectable.

Once an herbicidal compound is identified that inhibits function of the wild-type enzyme, thus killing the organism containing the enzyme, resistant mutants can be isolated by mutagenizing a population of the organism in question, growing the mutagenized population in the presence of a concentration of the inhibitor sufficient to inhibit growth of the wild-type organism, and selecting individuals from the population that are able to grow more rapidly than wild-type organisms.

Mutagenesis in vivo can be by any of several means, including chemical, e.g., ethyl methanesulfonate [Miller, *Experiments in Molecular Genetics,* Cold Spring Harbor Laboratory, Cold Spring Harbor, N.Y. (1972); Davis et al. *Advanced Bacterial Genetics,* Cold Spring Harbor Laboratory, Cold Spring Harbor, N.Y. (1980); Sherman et al., *Methods in Yeast Genetics,* Cold Spring Harbor Laboratory, Cold Spring Harbor, N.Y. (1983); and Somerville and Ogren, In Edelman et al. (eds) *Methods in Chloroplast Molecular Biology,* Elsevier Biomedical Press, pp. 129-138 (1982)], ultraviolet mutagenesis [Miller, *Experiments in Molecular Genetics,* Cold Spring Harbor Laboratory, Cold Spring Harbor, N.Y. (1972)], X-ray mutagenesis (e.g., Hake and Freeling, Nature 320, 621-623 (1986); and Poethig, Nature 336, 82-83 (1988)] and gamma irradiation. Alternatively, the sequence encoding histidinol dehydrogenase can be mutagenized in vitro by any of several chemical or enzymatic treatments [e.g., Zoller and Smith, Meth. Enzymol. 100, 468-500 983); Leung et al., Technique 1:11-15 (1989); and Shortle and Bolstein, Method. Enzymol. 100:457-468 (1983)]. Such mutated sequences are re-introduced into the host organism, preferably a microbe, and the population containing a mixture of reintroduced mutated sequences is grown on a toxic concentration of the inhibitor. Individuals are directly selected for their ability to grow in the presence of this toxic amount of inhibitor, which ability is conferred by the introduced mutated sequence.

The mutant individuals that result from in vivo mutagenesis, having an ability to tolerate normally toxic concentrations of the inhibitor, can be identified and genetically purified (either by streaking to single colonies several times for the case of a microbe, or by repeatedly selecting a single seed, growing to maturity, and self-pollinating for the case of a plant), the gene encoding histidinol dehydrogenase can be rapidly isolated from the mutant by the polymerase chain reaction and its DNA sequence determined and translated into a predicted amino acid sequence. Amino acids found in the mutant to differ from wild type can be assumed to be responsible for the inhibitor-resistant phenotype. Preferably, the causal nature of the amino acid changes can be directly tested by expressing the mutated sequence in a microbial or plant system, and demonstrating that introduction of the mutated sequence is sufficient to confer an inhibitor-resistant phenotype on an otherwise wild-type individual.

An assay to identify inhibitor-resistant histidinol dehydrogenase mutants comprises:

(a) incubating a first sample of histidinol dehydrogenase and its substrate in the presence of a second sample comprising a histidinol dehydrogenase inhibitor;

(b) measuring an unmutated reactivity of the histidinol dehydrogenase from step (a);

(c) incubating a first sample of a mutated histidinol dehydrogenase and its substrate in the presence of a second sample comprising a histidinol dehydrogenase inhibitor;

(d) measuring a mutated reactivity of the mutated histidinol dehydrogenase from step (c); and (e) comparing the mutated reactivity to the unmutated reactivity of the histidinol dehydrogenase.

The reaction mixture and the reaction conditions are the same as for the assay to identify inhibitors of histidinol dehydrogenase (inhibitor assay) with the following modifications. First, a histidinol dehydrogenase mutant, obtained as described above, is substituted in one of the reaction mixtures for the wild-type histidinol dehydrogenase of the inhibitor assay. Second, an inhibitor of wild-type histidinol dehydrogenase is present in both reaction mixtures. Third, mutated reactivity (enzyme activity in the presence of inhibitor and mutated histidinol dehydrogenase) and unmutated reactivity (enzyme activity in the presence of inhibitor and wild-type histidinol dehydrogenase) are compared to determine whether a significant increase in enzyme activity is observed in the mutated reactivity when compared to the unmutated reactivity. Mutated reactivity is any measure of enzymatic activity of the mutated histidinol dehydrogenase enzyme while in the presence of a suitable substrate and the inhibitor. Unmutated reactivity is any measure of enzymatic activity of the wild-type histidinol dehydrogenase enzyme while in the presence of a suitable substrate and the inhibitor. A significant increase is an increase in enzymatic activity that is larger than the margin of error inherent in the measurement technique, preferably an increase by about 2-fold of the activity of the wild-type enzyme in the presence of the inhibitor, more preferably an increase by about 10-fold, most preferably an increase by about 100-fold.

A mutated histidinol dehydrogenase-encoding DNA sequence that confers herbicide resistance can then be introduced into a crop species of interest, allowing the crop to survive in the presence of a concentration of the herbicide that kills all plants lacking the resistant form of the enzyme.

The coding DNA sequence to be introduced into the plant cell can be introduced into the plant cell in a number of ways that are well known to those of skill in the art. For example, methods of transforming plant cells include microinjection (Crossway et al., BioTechniques 4:320-334 (1986)], electroporation (Riggs et al., Proc. Nat. Acad. Sci. USA 83:5602-5606 (1986)], Agrobacterium mediated transformation (Hinchee et al. Biotechnology 6:915-921 (1988)], direct gene transfer (Paszkowski et al., EMBO J. 3:2717-2722 (1984)], and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6:923-926 (1988)]. Also see, Weissinger et al., Annual Rev. Genet. 22:421-477 (1988); Sanford et al., Particulate Science and Technology 5:27-37 (1987)(onion); Christou et al., Plant Physiol. 87:671-674 (1988)(soybean); McCabe et al., Bio/Technology 6:923-926 (1988)(Soybean); Datta et al., Bio/Technology 8:736-740 (1990)(rice); Klein et al., Proc. Nat. Acad. Sci. USA 85:4305-4309 (1988)(maize); Klein et al, Bio/Technology 6:559-563 (1988)(maize); Klein et al., Plant Physiol. 91:440-444 (1989)(maize); Fromm et al., Bio/Technology 8:833-839 (1990); Gordon-Kamm et al., Plant Cell 2:603-618 (1990)(maize); and Pace et al., copending U.S. patent application Ser. No. 573,105, filed Aug. 24, 1990, entitled Production of Transgenic Elite Maize Plants and Their Progeny (elite maize).

Transformation of the plant cells includes separating transformed cells from those that have not been transformed. One convenient method for such separation or selection is to incorporate into the material to be inserted into the transformed cell a gene for a selection marker. As a result, only those cells that have been successfully transformed will contain the marker gene. The translation product of the marker gene will then confer a phenotypic trait that will make selection possible. Usually the phenotypic trait is the ability to survive in the presence of some chemical agent, such as an antibiotic, e.g., kanamycin, G418, paromomycin, etc., which is placed in a selection media.

Once the transformed plant cells have been cultured on the selection media, surviving cells are selected for further study and manipulation. Selection methods and materials are well known to those of skill in the art, allowing one to choose surviving cells with a high degree of predictability that the chosen cells will have been successfully transformed with exogenous DNA.

After transformation of the plant cell or plant, those plant cells or plants transformed by the Ti plasmid so that the enzyme is expressed, can be selected by an appropriate phenotypic marker. These phenotypical markers include, but are not limited to, antibiotic resistance. Other phenotypic markers are known in the art and may be used in this invention.

All plants from which protoplasts can be isolated and cultured to give whole regenerated plants can be transformed by the present invention so that whole plants are recovered which contain the DNA coding sequence. Some suitable plants include, for example, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersion, Nicotiana, Solanum, Petunia, Dactylis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghum and Datura.

There is an increasing body of evidence that practically all plants can be regenerated from cultured cells or tissues, including but not limited to, all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been successful recently (Hooykas-Van Slogteren et al., Nature 311:763-764 (1984)]. There is growing evidence now that certain monocots can be transformed by Agrobacterium. Using current experimental approaches that have now become available, cereal and grass species may be transformable.

Additional plant genera that may be transformed by Agrobacterium include Ipomoea, Passiflora, Cyclamen, Malus, Prunus, Rosa, Rubus, Populus, Santalum, Allium, Lilium, Narcissus, Ananas, Arachis, Phaseolus and Pisum.

Plant regeneration from cultural protoplasts is described in Evans et al., "Protoplast Isolation and Culture," in *Handbook of Plant Cell Culture* 1:124-176 (MacMillan Publishing Co., New York 1983); M. R. Davey, "Recent Developments in the Culture and Regeneration of Plant Protoplasts," Protoplasts 1983); P. J. Dale, "Protoplast Culture and Plant Regeneration of Cereals and Other Recalcitrant Crops," in Protoplasts 1983—Lecture Proceedings, pp. 31-41 (Birkhauser, Basel, 1983); and H. Binding, "Regeneration of Plants," in *Plant Protoplasts*, pp. 21-37 (CRC Press, Boca Raton, 1985).

Regeneration varies from species to species of plants, but generally a suspension of transformed protoplasts containing multiple copies of the toxin gene is first provided. Embryo formation can then be induced from the protoplast suspensions, to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed to produce an inbred plant. The inbred plant produces seed containing the hybrid gene. These seeds can be grown to produce plants that have the hybrid gene. Such transformed plants and seeds are known as transgenic plants and seeds. Preferred transgenic plants are transgenic crops, which are plants suitable for human cultivation, more preferably plants all or part of which are fit for consumption by animals raised as a source of human food, e.g., livestock, poultry, fish, etc.

Such transformed seeds can then be used to improve crop yields by growing transformed plants from the transformed seeds in the presence of a histidinol dehydrogenase inhibitor that would be herbicidal to non-transformed plants growing among the transformed crops (i.e., weeds). Genetically engineering crops in this fashion to become resistant to a herbicide with no vertebrate toxicity would encourage the use of safe herbicides on this type as an alternative to more broadly toxic herbicides of questionable environmental safety and vertebrate toxicity.

The active ingredients of the present invention are normally applied in the form of compositions together with one or more agriculturally acceptable carriers, and can be applied to the crop area or plant to be treated, simultaneously or in succession, with further compounds. These compounds can be both fertilizers or micronutrient donors or other preparations that influence plant growth. They can also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying active ingredients of the present invention or an agrochemical composition which contains at least one of the active ingredients is leaf application. The number of applications and the rate of application depend on the intensity of infestation by the corresponding weed. However, the active ingredients can also penetrate the plant through the roots via the soil (systemic action) by impregnating the locus of the plant with a liquid composition, or by applying the compounds in solid form to the soil, e.g. in granular form (soil application). The active ingredients may also be applied to seeds (coating) by impregnating the seeds either with a liquid formulation containing active ingredients, or coating them with a solid formulation. In special cases, further types of application are also possible, for example, selective treatment of the plant stems or buds.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare ("ha", approximately 2.471 acres), preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants re nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one $C_8$-$C_{22}$ alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

The agrochemical compositions usually contain from about 0.1 to about 99%, preferably about 0.1 to about 95%, and most preferably from about 3 to about 90% of the active ingredient, from about 1 to about 99.9%, preferably from about 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

Whereas commercial products are preferably formulated as concentrates, the end user will normally employ dilute formulations.

EXAMPLES

The following examples are intended to exemplify specific embodiments of the present invention without limiting the scope in any way.

EXAMPLE 1

Materials and Strains

Sepharose-4B is purchased from Pharmacia LKB. Histidinol dihydrochloride is from Aldrich (Milwaukee, Wis.), and NAD+, sodium metaperiodate, epichlorohydrin and nitroblue tetrazolium are from Sigma (St. Louis, Mo.). Sodium cyanoborohydride is purchased from Nakarai, and phenazine methosulfate from Wako Pure Chemical Industries (Osaka, Japan). All other chemicals used are of analytical grade.

Cabbage (*Brassica oleracea*), cucumber (*Cucumis sativus*), asparagus (*Asparagus officinalis*), eggplant (*Solanum melongena*), lettuce (*Lactuca saliva*), and pimento (*Capsicum annum*) are cultivated in a growth chamber with 16 h/8 h light/dark cycle at 25° C. during illumination period and 15° C. during dark period. The relative humidity is constant at 80%. Cell cultures of Rosa "Paul's Scarlet" are a gift of Andre Strauss, CIBA-GEIGY Ltd., Switzerland, and cultured in suspension as previously described [Strauss et al, Planta 163:554–562 (1985)]. Cell cultures of tobacco (Nicotiana tabacum L. cv Samsun NN) and suspension cultures of wheat (Triticum aestivum var Chinese Spring) are kindly provided by Yaguyuki Yamanda, Kyoto University, Japan, and grown as described elsewhere [Kumpaisal et al., Plant Physiol. 85:145–151 (1987); and Yamada and Sato, Plant & Cell Physiol. 19:691–699 (1978)]. Mature spring cabbage (*Brassica oleracea L. var capitata L.*) is purchased from a local grocer. Wheat germ is obtained from Sigma (St. Louis, Mo.).

EXAMPLE 2

Preparation of Enzyme Extract

Two week old plants, whole cabbage heads or well grown cell tissues are used as the enzyme sources. The plant material is homogenized with a Polytron blender in cold 100 mM sodium phosphate buffer, pH7.2 (buffer A), and the homogenate passed through a filtration cloth. After centrifugation at 30,000×g for 20 min, the supernatant is fractionated with 45–60% saturation of ammonium sulfate on ice. The precipitate is collected by centrifugation, dissolved in buffer A and the solution desalted on Sephadex G-25. This protein enriched extract is used for the determination of histidinol dehydrogenase activity in various plants.

EXAMPLE 3

Purification of Histidinol Dehydrogenase

Spring cabbage heads are homogenized using a kitchen mixer and suspension processed as described above, except that desalting is performed by extensively dialyzing against 50 mM Tris/HCl buffer, pH7.4 (buffer B). All subsequent procedures are carried out at 4° C.

Dialyzed protein extract is applied to a DEAE-Toyopearl column equilibrated with buffer B. After washing the column with buffer B, protein is eluted with a linear gradient of buffer B containing sodium chloride (0–500 mM). The protein fraction with activity is eluted from the DEAE-Toyopearl column before the main protein peak, at a concentration of 150 mM sodium chloride in the buffer.

Fractions containing enzyme activity are pooled and directly applied to a histidinol-Sepharose-4B column (2.5×8 cm) (EXAMPLE 7) at a flow rate of 36 ml/h. Unabsorbed protein is eluted by extensively washing with 10 mM Tris/HCl buffer, pH 7.3 containing 140 mM NaCl (buffer C). Bound histidinol dehydrogenase is eluted with 50 mM Tris/HCl, pH 7.3 containing imidazole.

Several unsuccessful attempts were made to purify histidinol dehydrogenase from mature spring cabbage heads by conventional purification methods. The development of an affinity gel, highly specific for this enzyme finally made it possible to purify the protein in three steps with a high yield to apparent homogeneity (Table I). All activity is bound to the gel, probably very tightly, since only 40% of the activity could be eluted specifically with a one step addition of high concentration of imidazole (700 mM) in the elution buffer (FIG. 1). By this step alone, the specific enzyme activity is increased by a factor of 350 to 10.16 U/mg of protein, showing this chromatography to be very specific for histidinol dehydrogenase. The over-all 2116-fold purification does not include the first step of fractionated ammonium sulfate precipitation, since no activity could be detected in crude extract. A heavily loaded SDS polyacrylamid gel showed one major band.

TABLE I

Purification of histidinol dehydrogenase. In this typical purification, 10 kg of cabbage heads are processed. All activities are measured after desalting with either Sephadex G-25 or dialysis. The activity in the crude extract could not be detected (n.d.).

| Purification step | Total protein mg | Total activity U | Recovery % | Specific activity U/mg | Purity-fold |
|---|---|---|---|---|---|
| Crude extract | n.d. | n.d. | n.d. | n.d. | n.d. |
| Ammonium sulfate fractionation | 4750 | 23 | 100 | 0.0048 | 1 |
| DEAE-Toyopearl ion-exchange chromatography | 560 | 20.1 | 87 | 0.029 | 6 |
| Histidinol-Sepharose-4B affinity chromatography | 0.75 | 7.6 | 33 | 10.16 | 2116 |

After desalting all fractions on Sephadex G-25, the enzyme activity in each fraction is determined. Active fractions are pooled and concentrated on an Amicon ultrafiltration membrane (YM-10). This enzyme preparation is stored at −80° C. and used for all experiments, except for the activity screening in plants.

Storage of the enzyme for more than 4 months at −80° C. did not change significantly the activity. At 4° C., the enzyme lost 10% of its activity during one week. By the addition of glycerol to a final concentration of 20%, full activity could be maintained at 40° C. for more than one week.

EXAMPLE 4

Gel Filtration

A Sepharose 12 column (Pharmacia LKB, Piscataway, N.J.) is equilibrated with purification buffer C at room temperature. Samples of purified enzyme are applied to the column and eluted with buffer C at a flow rate of 0.5 ml/min. The molecular mass is calculated using a molecular weight marker kit (Sigma, St. Louis, Mo.). The native molecular weight of the enzyme is determined by Superose 12 gel filtration to be 103,000.

EXAMPLE 5

Polyacrylamide Gel Electrophoresis

SDS-polyacrylamide gel electrophoresis is performed as described elsewhere [Laemmli, Nature 227:680–685 (1970)], using 10–20% acrylamide. Proteins in sample buffer are put in a heating block at 100° C. for 10 min. For the calculation of the molecular mass of denatured and reduced protein, an electrophoresis calibration kit for molecular weight determination (Pharmacia, Piscataway, N.J.) is used. Under denaturing and reducing conditions, the enzyme migrated as a single band of 52 kdaltons if exposed to SDS-polyacrylamide gel electrophoresis, suggesting a dimeric quaternary structure of the enzyme.

The molecular weight of 103,000 of native cabbage enzyme is considerably higher than that of the enzyme from S. typhimurium (82,000 [Burger et al., Biochem. J. 181:771–774 (1979)] and 90,000 [Eccleston et al., J. Biol. Chem. 254:11399–11404 (1979)]). The enzymes from cabbage and S. typhimurium are each composed of two subunits with a similar molecular weight of 52,000 and 43,000 [Burger et al., Biochem. J. 181:771–774 (1979)], respectively. However, the subunit molecular weight of the trifunctional enzyme from S. cerevisiae is calculated from the nucleotide sequence to be 87,935 [Donahue et al., Gene 18:47–59 (1982)] and estimated on SDS gels as about 95,000 [Keesey et al., J. Biol. Chem. 254:7427–7433 (1979)]. According to these data, the enzymes from yeast, S. typhimurium and cabbage differ significantly in their molecular weights.

EXAMPLE 6

Isoelectric Focusing

PhastGel (Pharmacia LKB, Piscataway, N.J.) with a ph-range of 4–6.5 is used for isoelectric focusing, performed on a Phast System (Pharmacia LKB, Piscataway, N.J.) according to the instruction manual of the supplier. The isoelectric point of the protein is determined using an isoelectric point calibration kit (Pharmacia LKB, Piscataway, N.J.).

The exposure of purified enzyme to analytical isoelectric focusing lead to its separation into six protein bands within the ph-range 5.1–5.4. Five bands showed histidinol dehydrogenase activity by employing activity staining. The sixth band had only very slight or no activity. In control experiments lacking either histidinol or NAD+ in the reaction mixture, p-nitro blue tetrazolium is not reduced to formazan. The activity of each of the five bands correlated with their colour intensities obtained by protein staining.

To rule out artifacts of the purification procedure, several independent purifications are carried out, starting from cabbage heads in different growth stages. In all cases, six protein bands are obtained.

EXAMPLE 7

Preparation of Histidinol-Sepharose-4B Gel

Sepharose-4B is activated with epichlorohydrin as previously described (Matsumoto et al., J. Biochem. 85:1091–1098 (1979)]. Epoxyactivated Sepharose-4B gel is suspended in 0.1N NAOH containing 0.5 g glucose per g of gel and incubated at 40° C. on a shaker for 24 h [Kanamori et al., J. Chromatog. 363:231–242 (1986). After washing extensively with water, the gel is suspended in prechilled sodium metaperiodate and the suspension shaken for 1 h at 4° C. The gel is washed with water, suspended in 0.1M HCl and incubated at room temperature for 1 h. Again, the gel is washed extensively with water, followed by thorough washing with 10 mM sodium phosphate buffer, pH 7.0 at room temperature.

The formyl carrier gel is suspended in 10 mM sodium phosphate buffer, pH 7.0 containing 100 mM of histidinol dihydrochloride, which is previously neutralized with NAOH, and the suspension incubated at 4° C. overnight. Five milligrams of sodium cyanoborohydride per g of gel is then added to the suspension and incubated with shaking at room temperature for 6 h. The gel is extensively washed with distilled water and treated with 5 mg sodium borohydride per g or gel for 3 h at 4° C. to convert the remaining formyl groups into hydroxymethyl groups.

EXAMPLE 8

Enzyme Assay

The enzyme activity is assayed spectrophotometrically by measuring the increase in absorbance at 340 nm due to the reduction of NAD+ in a Hitachi U-3120 spectrophotometer. The reaction mixture contained 150 mM Gly/NaOH buffer, pH9.2, 0.5 mM, $MnCl_2$, 2 mM NAD +, 5 mM histidinol, and 2-5 mU of enzyme sample in total volume of 0.5 ml. The reaction is started with the addition of histidinol, and incubated at 30° C. A reference sample containing water instead of histidinol is always run. One unit of enzyme catalyzing the formation of 2 μmol of NADH per min under the assay conditions.

In some experiments the activity is also followed by measuring the formation of His with a Hitachi L-850 amino acid analyzer. The enzyme reaction is terminated with formic acid (final concentration, 30%). The sample is then evaporated, and the precipitate dissolved in 0.2N HCl. This preparation is used for His analysis.

Distribution of Histidinol Dehydrogenase in eleven plant species or preparations are examined for histidinol dehydrogenase activity. Enzyme activity could not be detected in any crude extract, but is found in enriched extracts from various monocotyledon and dicotyledon species (Table I). Cultured rose cells and spring cabbage showed the highest specific enzyme activities. Wheat germ had an extremely high extractable activity probably due to its low content of water, however, its specific activity is modest. Also shoots of cabbage and cucumber, and spring cabbage heads contained a high extractable activity. No activity could be detected in 2 week old pimento shoots and cultured tobacco cells.

Histidinol dehydrogenase in microorganisms catalyzes the two last reactions to form the endproduct His. To verify this catalytic role for the isolated protein from cabbage, its catalyzed reaction is analyzed stoichimetrically with regard to His formation and NAD+ reduction. The amount of enzymatically produced NADH is determined from the absorbence at 340 nm, using the absorbence coefficient of 6220. The other formed product is identified by amino acid analysis as His. Authentic His added to reacted sample is co-eluted with enzymatically formed His. Neither His nor NADH are formed in the absence of NAD+, histidinol, or by using cooked enzyme. Two moles of NADH are formed for 0.99 mole of His after a reaction time of 2 min. (Table III). The formation of both products histidine and NADH is time dependent and correlated.

Figure 2:
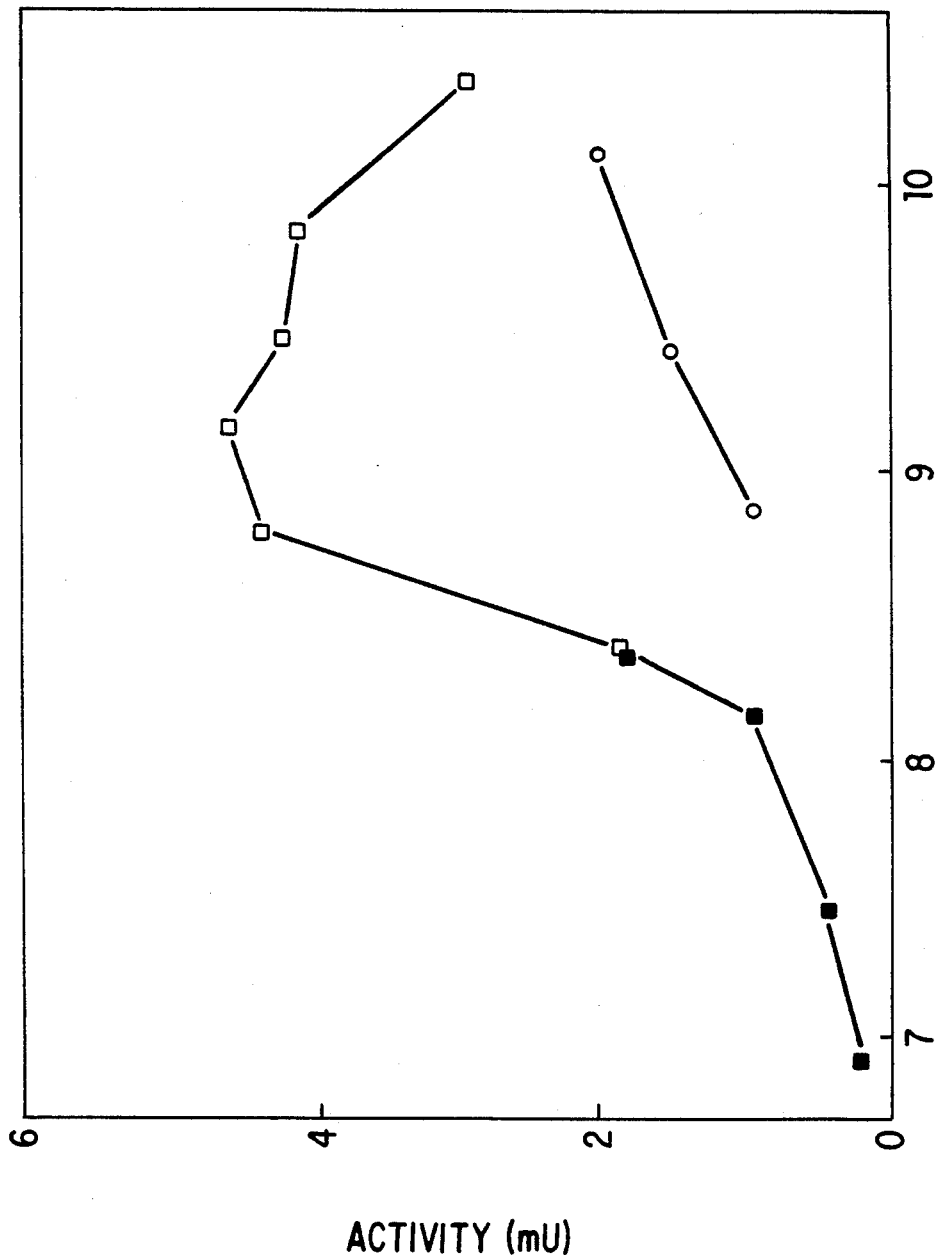
FIG. 2: Dependency of histidinol dehydrogenase activity on pH. (■) reaction in 50 mM HEPES buffer; (○) reaction in 50 mM Gly/NaOH buffer; (□) reaction in 50 mM CHES buffer. In all buffers, 0.5 mM $MnCl_2$ was included. The reaction was performed under standard conditions as described in Materials and Methods. In 50 mM phosphate buffer, pH7.5, no activity was detected.

Optimum pH for the activity is at 9.2 in 50 mM Gly/NaOH buffer (FIG. 2). At pH values below 9, activity decreased in either Gly/NaOH buffer or in 50 mM HEPES buffer. At pH9.2-10, almost full activity is maintained, but above 10, a rapid loss of activity occurred.

The apparent $K_m$ values of the enzyme for L-histidinol and NAD+ are determined under standard assay conditions such as 15.5 and 42 μM, respectively.

The influence of divalent metal ions on the enzyme reaction is shown in Table IV. The reaction is stimulated 26% by the addition of $Mn^{2+}$ compared to control conditions without the addition of any divalent metal ion to the reaction buffer (150 mM Gly/NaOH, pH9.2). The addition of $Ba^{2+}$, $Mg^{2+}$, $Ni^{2+}$, $C^{2+}$, $Zn^{2+}$ and $Cu^{2+}$ caused inhibition of the reaction.

Histidinol dehydrogenase from cabbage is the first His biosynthesis enzyme that has been purified to homogeneity from higher plants. By using a new affinity chromatography, the purification of this enzyme and its investigation became possible. Direct evidence that the purified protein is histidinol dehydrogenase is obtained from activity staining of the protein on the gel after isoelectic focusing. The enzymatically formed product starting from histidinol is identified as His. His and NADH are produced stoichiometrically, showing the same reduction of 2 mole of NAD+ for 1 mole of formed His as previously described for this reaction in microorganisms [Adams, J. Biol. Chem. 217:325-344 (1955)]. The present results demonstrate that the last two reaction steps in the His biosynthetic pathway in cabbage are identical to those in microorganisms and are catalyzed by the same single enzyme. The $K_m$ of this enzyme for L-histidinol (15.5 μm at pH 9.2) is very similar to those (16 and 8.8 μm) of the pure enzyme from S. typhimurium [Burger et al., Eur. J. Biochem. 116:137-142 (1981)] and the partially purified one from wheat germ (Wong and Mazelis, Phytochem. 20:1831-1834 (1981)]. The $K_m$ (42 μM) for NAD+ is considerably lower than that of the enzymes from S. typhimurium (1 mM) (24) and from wheat germ (140 μM, using partially purified enzyme (Wong and Mazelis, Phytochem. 20:1831-1834 (1981)]). The ph-optimum of the reaction between pH 9.2-9.4 is identical to that of histidinol dehydrogenase from other organisms. No other divalent metal ion than $Mn^{2+}$ showed a stimulation of the enzyme activity. This is in line with the results obtained with the enzyme from S. typhimurium, whose catalyzed reaction is also stimulated in the presence of $Mn^{2+}$ [Grubmeyer et al., Arch. Biochem. Biophys. 272:311-317 (1989)].

TABLE II

Distribution of histidinol dehydrogenase in different plant species and preparations. For the calculation of the extractable activity, the wet weight of the plant material is used. The weight of cells from suspension tissue cultures is determined after collection by filtration with a cloth. *) mU/mg: units of activity per mg. of protein; **) mU/g: units of activity per g of plant material.

| Plant source | Specific Activity (mU/mg*) | Extractable Activity (mU/mg**) |
|---|---|---|
| Cabbage shoots (Brassica oleracea L. var capitata L.) | 1.6 | 3.3 |
| Aparagus shoots (Asparagus officinalis) | 0.9 | 1.6 |
| Lettuce shoots (Lactuca sativa) | 0.4 | 0.3 |
| Egg plants shoots (Solanum melonena) | 0.4 | 0.9 |
| Cucumber shoots (Cucumis sativus) | 0.3 | 3.3 |
| Pimento shoots (Capsicum annum) | 0 | 0 |
| Spring cabbage (Brassica oleracea L. car capitata L.) | 6.1 | 2.8 |
| Wheat germ | 2.1 | 91 |
| Wheat cell culture (Triticum aestivum var Chinese Spring) | 0.5 | 0.4 |
| Rose cell culture (Rosa "Paul's Scarlet") | 6.2 | 0.9 |
| Tobacco cell culture (Nicotiana tabacum L. cv Samsun (NN) | 0 | 0 |

TABLE III

Stoichiometry of histidinol dehydrogenase reaction with regard to the formation of His and NAD+. The enzyme reaction is stopped after 2, 5 and 30 min reaction time and the sample analyzed by automated amino acid analysis. Histidinol does not react with ninhydrin and cannot be analyzed by amino acid analysis (at 50 nmole).

Reaction time   His concentration   NADA concentration

TABLE III-continued

| min | µmole/ml (a) | µmole/ml (b) | b/a |
|---|---|---|---|
| 0 | 0 | 0 | — |
| 2 | 17.6 | 35.6 | 2.02 |
| 5 | 36.6 | 80.0 | 2.18 |
| 30 | 143.7 | 316.0 | 2.2 |

TABLE IV

Effect of divalent metal ions on histidinol dehydrogenase activity. The concentration of metal ion is 0.5 mM. The activity is determined after 3 min reaction time, while the velocity is still constant.

| Addition | Relative Activity % |
|---|---|
| None | 100 |
| $Mn^{2+}$ | 126 |
| $Ba^{2+}$ | 65 |
| $Mg^{2+}$ | 54 |
| $Ni^{2+}$ | 46 |
| $Ca^{2+}$ | 36 |
| $Zn^{2+}$ | 34 |
| $Cu^{2+}$ | 24 |

EXAMPLE 9

Activity Staining

Isoelectric point calibration proteins and purified enzyme (in quadruplicate) are applied on a PhastGel (pH-range 4–6.5) to give five lanes. After running the isoelectric focusing, the gel is cut into four pieces. The one containing marker proteins in addition to enzyme is stained with Coomassie Brilliant Blue R250. Another piece of gel containing only enzyme is subjected to activity staining as described elsewhere [Skyring et al., Anal. Biochem., 36:511–520 (1970)], with a slight modification. The gel is immersed in 10 ml of reaction mixture containing 5 mM histidinol and 2 mM NAD+. By the addition of 150 µl of nitroblue tetrazolium and 150 µl of phenazine methosulfate to give a final concentration of 0.5 mM and 0.13 mM, respectively, the staining process is started. Incubation is carried out at 30° C. for 30 min. Two other pieces of gel containing only enzyme are identically incubated, but either without histidinol or without NAD+.

EXAMPLE 10

Protein Determination

The concentration of the protein is determined by Bradford protein assay method using bovine serum albumin as a standard [Bradford, Anal. Biochem. 72:248–254 (1976)].

EXAMPLE 11

Amino Acid Sequencing

Approximately 50 µg purified histidinol dehydrogenase is dried and resuspended in 0.1% trifluoroacetic acid and is subjected directly to automated Edman degradation with an Applied Biosystems 477A gas-liquid-phase protein sequencer (Strickler et al., Anal. Biochem. 140:553–566 (1984)]. The phenylthiohydantion (PTH) amino acid derivatives are separated and identified with an on-line PTH analyzer (Applied Biosystems, Foster City, Calif.) with PTH-Cl8 column.

The first sequence run showed a recovery of 15% of the protein concentration determined by amino acid analysis, indicating that 85% of the N-terminus is blocked for unknown reason. The first N-terminal amino acid of the 15% of unblocked enzyme could not be determined unambiguously in both experiments. Ala and Lys are found most abundantly, but also Ser, Gly, Glu, Val and Leu are detected, all in similar concentrations.

The remainder of the N-terminal amino acid sequence is determined to be:

M K I Y R L S E L S F ? Q V E N L K A R ? I D where question marks indicate residues that could not be determined from the amino acid sequencing data.

A further 160 ug of purified histidinol dehydrogenase protein is dried and resuspended in 415 ul of 20 mM Tris-HCl, pH 8.0. Lysyl endopeptidase [EC 3.4.21.50; Wako Chemicals, Osaka, Japan) is added to achieve a final concentration of approximately 33 ug/ml. This is equivalent to a weight ratio of approximately 1:500, peptidase:protein substrate. The digestion is incubated at room temperature for 24 hours, and the resulting peptides are separated by reverse phase HPLC on an Aquapore RP-300 (C-8) column (2.1×220 mM). The column is eluted with a 45 minute linear gradient of 0–70% acetonitrile in 0.1% TFA at a flow rate of 220 ul/minute. Peptides eluting at 17, 18, 32, 45, and 48 minutes are collected and analyzed by automated Edman degradation as described above. The following amino acid sequences are obtained:

| Lys-C #17 | TELSFAK |
|---|---|
| Lys-C #18 | TVVLATPPTK |
| Lys-C #32 | EAFDVAYDNIYAFHLAQK |
| Lys-C #45 | KFMTVQSLTEEGLRNLGPYVA TMAEIEGLDA |
| Lys-C #48 | ALSHSFTVFARDMIEAITFSN LYAPEK |

A further 90 ug of purified histidinol dehydrogenase protein is dried and resuspended in 200 ul of 2% CNBR in 70% formic acid. The protein is digested at room temperature for 24 hours. The resulting peptides are purified exactly as described above, except that a 0–100% gradient of acetonitrle is used. Peptides eluting at 6 and 18 minutes are collected and subjected to amino acid sequencing by automated Edman degradation as described above. The following sequences are obtained:

| CNBr #6 | MAEIEGLDAHKRAVTLR?KDIE |
|---|---|
| CNBr #18 | LAIPAQIAGRKTVVLATP |

EXAMPLE 12

Obtaining the cDNA Sequence for Histidinol Dehydrogenase

Three oligonucleotides that correspond to portions of the above amino acid sequences are synthesized by automated phosphoramidite synthesis on an Applied Biosystems (Foster City, Calif.) Model 380B DNA Synthesizer.

Their sequences and the amino acid residues they correspond to are indicated below:

| EW25 | 5' TTAAGAATTCTAYGAYAAYATHTAYGC 3' |
|---|---|
| JR03 | 5' CCYTCDATYTCNGCCAT 3' |
| JR02 | 5' ATNGCYTCDATCATRTC 3' | where D indicates any the bases A, T, or G; H indicates the bases A, T, or C; R indicates the purines A or G; Y indicates the pyrimidines T or C. EW25 is a mixture of 48 oligonucleotides comprising all possible DNA sequences coding for the amino acid sequence Y D N I Y A, found within peptide Lys-C #32. JR03 is a mixture of 48 oligonucleotides comprising the complements of all possible DNA sequences coding for the amino acid sequence M A E I E G, found within both peptides Lys-C #45 and CNBR #6. JR02 is a mixture of 48 oligonucleotides comprising the complementary strands of all possible DNA sequences coding for the amino acid sequence D M I E A I, found within peptide Lys-C #48.

The sequences for the cabbage peptides are aligned with the translated sequence for the yeast HIS4C gene [Donahue et al., Gene 18:47-59 (1982)], which encodes histidinol dehydrogenase. The cabbage peptides are found to have approximately 45% identity to the yeast sequence in their shared regions. Using such an alignment, and assuming that the cabbage sequence is approximately co-linear with the yeast sequence, Lys-C #32 is found to lie upstream (i.e. toward the N-terminus of the protein) relative to Lys-C #45 and CNBR #6, which lie near the C-terminus of the protein approximately 320 amino acids downstream. Lys-C #48 is found to lie between these peptides. Thus, EW25 should be relatively near the 5' end of the cDNA, JR03 should be near the 3' end of the cDNA, and JR02 should lie between these oligonuceotides.

Total RNA is prepared from frozen cabbage leaf tissue by phenol extraction followed by lithium chloride precipitation as described by Lagrimini et al. [Proc. Natl. Acad. Sci. USA 84, 7542-7546 (1987)]. Poly-(A)+MRNA is isolated from the total RNA using a poly(A) quick MRNA isolation kit (Stratagene, La Jolla, Calif.) exactly as described in the manufacturer's instructions. The MRNA is enzymatically converted into cDNA and cloned in the lambda ZAP II vector using a ZAP-cDNA gigapack II gold synthesis kit (Stratagene, La Jolla, Calif.) using instructions supplied with the kit by the manufacturer. The resulting cDNA library is propagated and amplified as described by the manufacturer of the kit.

Total DNA is prepared from the library using the Lambdasorb reagent (Promega Biotech, Madison, Wis.) by the method described by the manufacturer. A polymerase chain reaction [PCR; Saiki et al., Science 239:487-491 (1988)] is performed using the library DNA as template, and EW25 and JR03 as primers. The reaction is performed in a total volume of 50 ul, with 10 ug of template DNA, 200 pmole of each primer mixture, 100 uM each of DATP, DCTP, DGTP, and DTTP, 1x PCR buffer supplied by the manufacturer (Perkin Elmer Cetus, Norwalk, Conn.) and 2.5u AmpliTaq DNA polymerase (Perkin Elmer Cetus). The reaction is cycled through the following temperature profile 40 times, in a DNA Thermocycler (Perkin Elmer Cetus): 94° C. for 45 seconds, 42° C. for 45 seconds, and 72° C. for 45 seconds. At each cycle, the 72° C. step is increased by 2 seconds.

The PCR products are separated on a 2% low-gelling-temperature agarose gel (Nu-Sieve, FMC BioProducts, Rockland, Me.). Several fragments are detected by ethidium bromide stain, one of which is approximately 975 bp in length, the approximate size expected. The gel is blotted to nylon membrane (GeneScreen Plus, NEN Research Products, Boston, Mass.) in 0.4 M NAOH as described by Reed and Mann (Nucleic Acids Res. 13:7207-7221 (1985)]. The gel blot is hybridized to the JR02 oligonucleotide mixture which has been $^{32}$P-labeled using T4 polynucleotide kinase (New England Biolabs, Beverly, Mass.) and gamma- 32 P ATP (New England Nuclear, Boston, Mass.). The approximately 975 bp fragment is specifically detected by the JR02 probe, strongly indicating that it comprises a portion of the cDNA for histidinol dehydrogenase.

The PCR fragment is excised from a low-gelling-temperature agarose gel, digested with EcoRI, and subcloned into the pbluescript plasmid (Stratagene, La Jolla, Calif.). The subcloned PCR insert is labeled with $^{32}$P by random priming using the PrimeTime kit (International Biotechnologies, New Haven, Conn.), and used to probe plaque lifts of the lambda ZAP II cabbage cDNA library described above. Positively-hybridizing plaques are purified and their inserts excised into the pbluescript plasmid in vivo using the method described by the manufacturer of the lambda ZAP II cloning vector (Stratagene, La Jolla, Calif.). The DNA sequences of the plasmid cDNA inserts are determined by the dideoxy method using the Sequenase kit (United States Biochemical, Cleveland, OH). One plasmid subclone, designated pBSACabHdH7, is found to contain a 1613 bp insert that encodes a predicted protein that matches the sequences of the peptides derived from histidinol dehydrogenase, including the N-terminal peptide, indicating a full-length, or nearly full-length cDNA (see, FIG. 3 for the DNA sequence).

EXAMPLE 13

Transformation of Maize by Microprojectile Bombardment of Friable, Embryogenic Culture of the Elite Genotype 0274 with the Genes for Histidinol Dehydrogenase, a Scorable Marker and a Selectable Marker The target is a friable, embryogenic culture of the Funk genotype 0274 (CIBA-GEIGY Seeds, Greensboro, NC). Each target contained approximately 250 milligrams of this culture plated onto Durapore filters, which are placed on top of the medium designated '2N63S'[N6 media of Chu et al., Scientia Sinica, Vol. XVIII(NO. 5):659-668 (1975) supplemented with 3 percent sucrose and 2 milligrams per liter of 2,4-dichlorophenoxyacetic acid). A 2X gene dose of GUS gene 'equivalents' of the plasmide pCHN1761 (as described in copending U.S. patent Ser. No. 573,105, filed Aug. 24, 1990, wherein the histidinol dehydrogenase gene is placed into the vector; or the histidinol dehydrogenase clones contained therein) and plasmids containing selectable markers such as phosphinothricin resistance, hygromycin resistance, paromomycin resistance or scorable markers such as glucouronidase (GUS) or luciferase are co-precipitated onto tungsten particles according to the CaCl$_2$- Spermidine precipitation method of Klein et al. (Proc. Nat. Acad. Sci. USA, 85:4305, 1988). Five microliters of the DNA-tungsten preparation is pipetted onto the macroprojectile and propelled toward the target using a number 1 gray cartridge essentially as described in the operating instructions for the bombardment device.

After 5 days, the cells are transferred to fresh filters and placed onto media containing selection agents at a concentration of 1 to 500 milligrams of per liter, depending on the agent used. The filters with the cells are transferred approximately weekly to fresh medium containing the selection agent. The concentration of the agent may be increased during the course of selection. After 6 weeks of selection, colonies appeared randomly on the filters. Colonies are isolated over the course of three weeks, each one being transferred to fresh medium containing the selection agent but without a filter for a secondary selection period.

We claim:

1. An isolated and purified DNA molecule consisting essentially of a DNA sequence encoding a higher plant histidinol dehydrogenase.

2. A DNA molecule according to claim 1, wherein said DNA sequence is substantially homologous to the DNA sequence of FIG. 3.

3. A DNA molecule according to claim 2, wherein said DNA sequence is homologous to at least 60 percent of the DNA sequence of FIG. 3.

4. A DNA molecule according to claim 3, wherein said DNA sequence is homologous to at least 75 percent of the DNA sequence of FIG. 3.

5. A DNA molecule according to claim 4, wherein said DNA sequence is homologous to at least 90 percent of the DNA sequence of FIG. 3.

6. A DNA molecule according to claim 1, wherein said DNA sequence is the DNA sequence of FIG. 3.

7. A purified and isolated DNA molecule consisting essentially of a DNA sequence encoding a higher plant histidinol dehydrogenase, wherein the protein is isolated by
   (a) exposing a protein extract to an ion exchange chromatography column to produce a first eluate in the presence of a linear gradient;
   (b) exposing the first eluate to an affinity chromatography column to produce a second eluate in the presence of a displacing solvent, wherein the affinity chromatography column comprises a ligand specific for histidinol dehydrogenase; and
   (c) storing the second eluate.

8. A DNA molecule of claim 1, wherein said DNA sequence is isolated from wheat.

* * * * *